(12) United States Patent
Behm

(10) Patent No.: US 6,644,321 B1
(45) Date of Patent: Nov. 11, 2003

(54) TACTILE FEEDBACK FOR INDICATING VALIDITY OF COMMUNICATION LINK WITH AN IMPLANTABLE MEDICAL DEVICE

(75) Inventor: Michael D. Behm, Chisago City, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/430,708

(22) Filed: Oct. 29, 1999

(51) Int. Cl.$^7$ .............................................. A61B 19/00
(52) U.S. Cl. ...................................... 128/899; 128/905
(58) Field of Search ............................... 607/30–32, 60, 607/27–29, 18, 19, 23, 22; 128/897–899, 903, 904; 340/870.05

(56) References Cited

U.S. PATENT DOCUMENTS

| | | | |
|---|---|---|---|
| 4,208,008 A | 6/1980 | Smith ........................... 371/15 |
| 4,233,985 A | 11/1980 | Hartlaub et al. ............. 128/419 |
| 4,236,524 A | 12/1980 | Powell et al. ................ 128/419 |
| 4,250,884 A | 2/1981 | Hartlaub et al. ............. 128/419 |
| 4,253,466 A | 3/1981 | Hartlaub et al. ............. 128/419 |
| 4,273,132 A | 6/1981 | Hartlaub et al. ............. 128/419 |
| 4,273,133 A | 6/1981 | Hartlaub et al. ............. 128/419 |
| 4,401,120 A | 8/1983 | Hartlaub et al. ............. 128/419 |
| 4,531,523 A | 7/1985 | Anderson .................... 128/419 |
| 4,794,392 A | 12/1988 | Selinko ....................... 340/825 |
| 4,821,723 A | 4/1989 | Baker, Jr. et al. ........... 128/419 |
| 5,052,388 A * | 10/1991 | Sivula et al. ................. 607/22 |
| 5,107,833 A | 4/1992 | Barsness ..................... 128/419 |
| 5,127,404 A | 7/1992 | Wyborny et al. ............ 128/419 |
| 5,131,388 A | 7/1992 | Pless et al. .................. 128/419 |
| 5,144,949 A | 9/1992 | Olson .......................... 128/419 |
| 5,158,078 A | 10/1992 | Bennett et al. .............. 128/419 |
| 5,199,428 A | 4/1993 | Obel et al. ................... 128/419 |
| 5,207,218 A | 5/1993 | Carpentier et al. .......... 128/419 |
| 5,226,413 A * | 7/1993 | Bennett et al. ................ 607/18 |
| 5,292,343 A | 3/1994 | Blanchette et al. ........... 607/32 |
| 5,312,453 A | 5/1994 | Shelton et al. ................ 607/19 |
| 5,314,430 A | 5/1994 | Bardy ............................ 607/5 |
| 5,324,315 A | 6/1994 | Grevious ...................... 607/60 |
| 5,330,507 A | 7/1994 | Schwartz ...................... 607/14 |
| 5,331,966 A | 7/1994 | Bennett et al. ............. 128/696 |
| 5,354,316 A | 10/1994 | Keimel ......................... 607/15 |
| 5,354,319 A * | 10/1994 | Wyborny et al. ............. 607/32 |
| 5,466,246 A * | 11/1995 | Silvian ......................... 607/32 |
| 5,476,488 A * | 12/1995 | Morgan et al. ............... 607/30 |
| 5,534,851 A | 7/1996 | Russek ....................... 340/573 |
| 5,545,186 A | 8/1996 | Olson et al. .................. 607/14 |
| 5,674,249 A * | 10/1997 | de Coriolis et al. ............ 607/5 |
| 5,709,225 A * | 1/1998 | Budgifvars et al. ......... 128/899 |
| 5,729,589 A | 3/1998 | Samson ....................... 379/34 |
| 5,733,313 A * | 3/1998 | Barreras, Sr. et al. ........ 607/33 |
| 5,843,139 A * | 12/1998 | Goedeke et al. .............. 607/32 |
| 5,861,018 A * | 1/1999 | Feierbach .................... 604/60 |
| 5,899,931 A * | 5/1999 | Deschamp et al. ........... 607/60 |
| 6,169,925 B1 * | 1/2001 | Villaseca et al. ............. 607/60 |
| 6,263,246 B1 * | 7/2001 | Goedeke et al. ............. 607/60 |

* cited by examiner

*Primary Examiner*—John P. Lacyk
*Assistant Examiner*—Nikita Veniaminov
(74) *Attorney, Agent, or Firm*—Girma Wolde-Michael; Paul H. McDowall; Thomas F. Woods

(57) ABSTRACT

Implantable medical device telemetry is provided between an implantable medical device and an external communication device. The implantable medical device includes a device transmitter and/or a device receiver. The external communication device includes a moveable communication head including an antenna therein connected to at least one of an external transmitter and/or an external receiver for communication with the device transmitter and/or the device receiver of the implantable medical device. A user moves the moveable head apparatus relative to the implantable medical device. Tactile feedback is provided to the user via the moveable head apparatus upon movement of the moveable head apparatus to a position where valid telemetry can be performed.

10 Claims, 11 Drawing Sheets

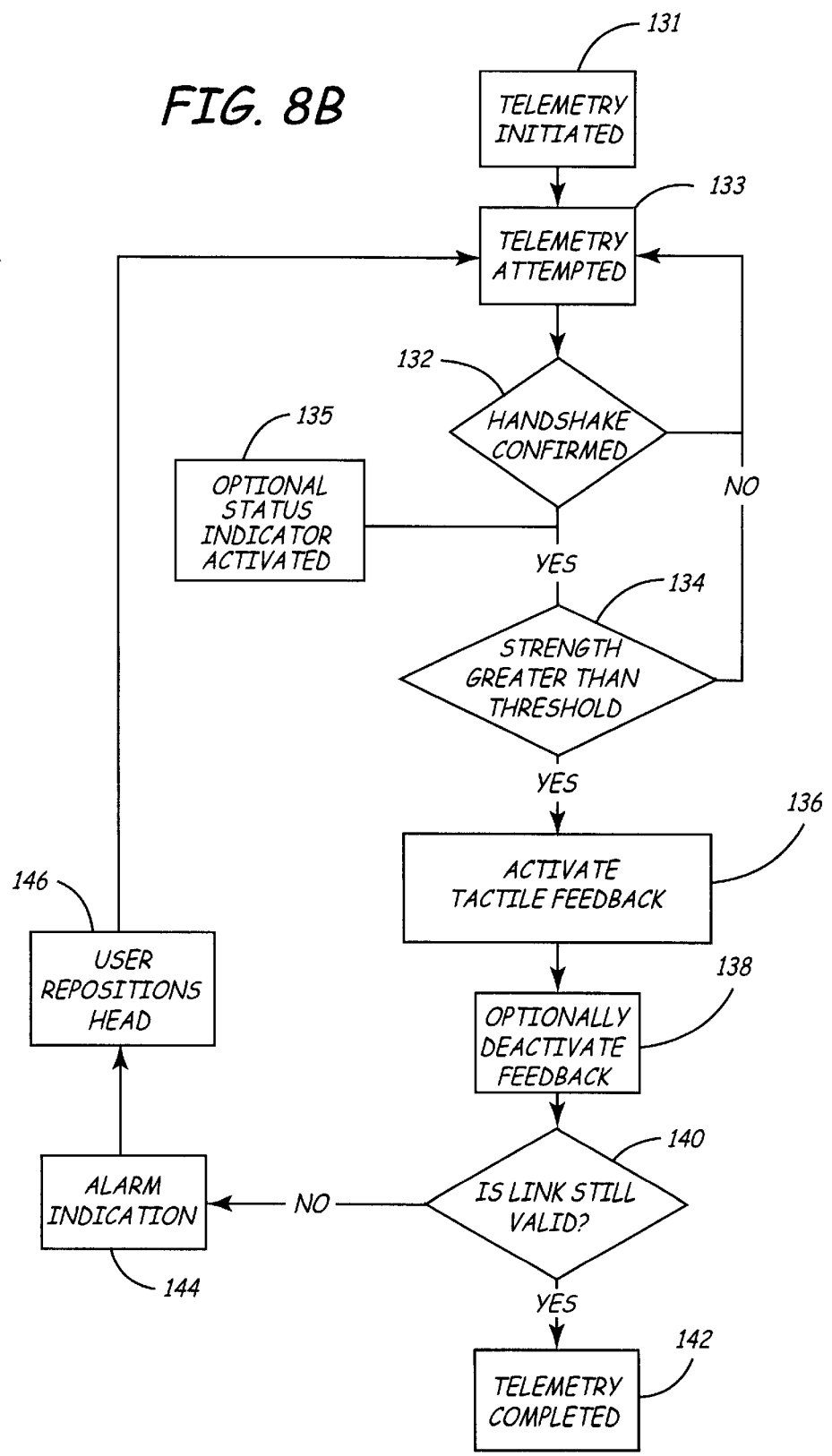

TACTILE FEEDBACK FOR INDICATING VALIDITY OF COMMUNICATION LINK WITH AN IMPLANTABLE MEDICAL DEVICE

FIELD OF THE INVENTION

The present invention relates to communication links with implantable medical devices. More particularly, the present invention pertains to techniques for indicating that such communication links are valid.

BACKGROUND OF THE INVENTION

In the field of implantable medical devices, such as cardiac pacemakers, tachyarrhythmia control devices, implantable drug dispensing devices, monitoring devices, and nerve stimulators, it has become common to provide a transceiver system for performing functions such as the remote programming and the telemetering of data out of the implanted device. For example, in such devices, it has become desirable to have the ability to reprogram the device's modes of operation, parameters, and other functions and/or to monitor the performance of such devices, both historically and contemporaneously. Generally, such implantable medical devices are designed to provide two-way telemetry by radio frequency signal transmission between the implanted medical device and a programming head or wand of an external communication device, e.g., external programmer apparatus, to provide for the exchange of coded transmitted information therebetween.

As the complexity of implantable medical devices increases over time, telemetry systems for enabling such implantable devices to communicate with external communication devices, e.g., programmers, has become more important. For example, it is desirable for a user, e.g., a physician, to noninvasively exercise some amount of control over the implantable medical device, e.g., to turn the device on or off after implantation, to adjust various parameters of the implantable medical device after implantation, etc.

Further, as implantable medical devices include more advanced features, it is typically necessary to convey correspondingly more information to the implantable medical device relating to the selection and control of such advanced features. For example, if a pacemaker is selectively operable in various pacing modes, it is desirable that a physician be able to noninvasively select a mode of operation. Further, for example, if a pacemaker is capable of pacing at various rates, or of delivering stimulating pulses of varying energy levels, it is desirable that the physician be able to select, on a patient-by-patient basis, appropriate values for such variable operational parameters.

Not only has the complexity of implantable medical devices led to the need to convey correspondingly more information to the implantable medical device, but it has also become desirable to enable the implanted medical device to communicate information outside of the patient to an external communication device, e.g., programmer. For example, for diagnostic purposes, it is desirable for the implanted device to be able to communicate information regarding its operational status to the physician. Various implantable medical devices are available which can transmit such information to an external communication device, e.g., the transmission of a digitized ECG signal for display, storage, and/or analysis by the external communication device.

As used herein, the term "uplink" and "uplink telemetry" will be used to denote the communications channel for conveying information from the implanted medical device to an external communication device, e.g., a programmer. Conversely, the term "downlink" and "downlink telemetry" will be used to denote the communications channel for conveying information from an external communication device to the implanted medical device.

Various telemetry systems for providing the necessary communication channels between an external communication device and an implanted medical device have been described. For example, typically, telemetry systems are employed in conjunction with an external programmer/processing unit. A programmer for noninvasively programming a cardiac pacemaker is described in the following U.S. Patents to Hartlaub, et al., each commonly assigned to the assignee of the present invention: U.S. Pat. No. 4,250,884, entitled "Apparatus for and Method of Programming the Minimum Energy Threshold for Pacing Pulses to be Applied to a Patient's Heart;" U.S. Pat. No. 4,273,132, entitled "Digital Cardiac Pacemaker with Threshold Margin Check;" U.S. Pat. No. 4,273,133, entitled "Programmable Digital Cardiac Pacemaker with Means to Override Effects of Reed Switch Closure;" U.S. Pat. No. 4,233,985, entitled "Multi-Mode Programmable Digital Cardiac Pacemaker;" U.S. Pat. No. 4,253,466, entitled "Temporary and Permanent Programmable Digital Cardiac Pacemaker;" and U.S. Pat. No. 4,401,120, entitled "Digital Cardiac Pacemaker with Program Acceptance Indicator." Aspects of the programmer that are the subject of the foregoing Hartlaub et al. patents are described in U.S. Pat. No. 4,208,008 to Smith, entitled "Pacing Generator Programming Apparatus Including Error Detection Means," and in U.S. Pat. No. 4,236,524 to Powell et al., entitled "Program Testing Apparatus."

Most commonly, telemetry systems for implantable medical devices employ a radio frequency (RF) transmitter and receiver in the implantable medical device, and a corresponding RF transmitter and receiver in the external communication device, e.g., programming unit. Within the implantable medical device, the transmitter and receiver use an antenna for receiving downlink telemetry signals and for radiating RF signals for uplink telemetry. For example, the radiating RF signals may be magnetically coupled through inductive (antenna) coils.

To communicate digital data using RF telemetry, a digital encoding scheme such as described in U.S. Pat. No. 5,127,404 to Wyborny et al., entitled "Improved Telemetry Format," is used. In particular, for example, in downlink telemetry a pulse interval modulation scheme may be employed wherein the external communication device, e.g., programmer, transmits a series of short RF "bursts" or pulses in which the duration of an interval between successive pulses, e.g., the interval from the trailing edge of one pulse to the trailing edge of the next pulse, encodes the data. For example, a shorter interval may encode a "0" bit while a longer interval may encode a "1" bit.

The external communication devices, e.g., programming devices, typically interface with the implanted medical device through the use of a programming head or paddle. For example, generally, the programming head or paddle is a hand-held unit adapted to be placed on or near the patient's body over the implant site of the patient's implanted medical device. The programming head may effect closure of a reed switch in the implantable medical device using a magnet to initiate a telemetry session. Thereafter, uplink and downlink communication may take place between the implanted medical device's transmitter/receiver and the receiver/transmitter of the external communication device. Other methods of initiating a telemetry session may also be used. For example, a wake-up pulse from an external communication device may be used to wake-up the implanted medical device which polls its downlink receiver at an appropriate interval.

For programming arrangements, and/or for monitoring arrangements, both uplink and downlink telemetry signal strength vary as a function of programming head positioning relative to the implantable device. In other words, the signal strength varies as a function of the coefficient of coupling between the communication head, e.g., programming head including an antenna configuration, and the implanted device. Therefore, it is important for the programming head to be properly positioned over the patient's implant site so that downlink RF signals can be detected in the implantable medical device and uplink signals can be detected by the programming head of the external communication device. For example, if the programming head is too far away from the implantable medical device, the attenuation of RF signals transmitted across the boundary of the patient's skin may be too great, preventing a telemetry link from being established.

As such, with appropriate feedback to a user, the user can position and reposition the programming head over the implant site until a suitable position is located to a establish a valid communication link between the external communication device a implanted medical device. Various feedback techniques have been used to indicate to a user when a programming head has been properly located over a patient's implanted medical device to establish a valid telemetry link.

For example, one technique used for determining when the programming head is properly positioned can be characterized as an "open loop" technique in that the determination of the correct head positioning is based solely upon an assessment of whether the uplink signal (i.e., the signal transmitted from the implanted medical device to the external communication device) meets some minimum requirement. In such an open loop verification system, adequate downlink signal strength is not tested. For example, an open loop system for determining the proper positioning of a programming head is described in U.S. Pat. No. 4,531,523 to Anderson, entitled "Digital Gain Control for the Reception of Telemetry Signals from Implanted Medical Devices."

A communication protocol using handshaking can also be used to verify that a minimum downlink field strength for detection in the implanted medical device exists to signal a physician that correct head positioning has been achieved. However, conventional handshaking protocols do not provide any information useable for optimization of head positioning to ensure an adequate operating margin. In other words, proper programming head positioning may be indicated even though the programming head is actually marginally positioned, such that a very slight shift in positioning (e.g., due to patient motion) results in downlink telemetry failure.

Further, closed loop systems have also been described for providing feedback to a user for positioning of the communication head for attaining a valid communication link with an implanted medical device.

For example, in U.S. Pat. No. 5,324,315 to Grevious, entitled "Closed-Loop Downlink Telemetry and Method for Implantable Medical Device," a specific type of downlink telemetry pulse is transmitted from the external communication device to the implanted medical device. In particular, the downlink pulses are bursts having a linear ramping envelope. The characteristics of the downlink burst envelope are such that the amplitude of the signal as detected by the implanted medical device's receiver, relative to the receiver's detection threshold, can be ascertained by measuring the time that the detected burst exceeds the receiver's detection threshold. This information can be communicated to the external communication device. In response to receipt of such information regarding the relative strength of the detected downlink signals, the external communication device can modulate the peak amplitude of the downlink burst envelopes by modulating the gain of the external communication device transmitter. As such, the external communication device can then ensure an adequate margin over the implanted medical device's detection threshold while at the same time avoiding the transmission of unnecessarily high energy downlink signals. As described therein, the downlink signal strength and/or the uplink signal strength can be used for activation of a telemetry status indication.

Generally, as described in U.S. Pat. No. 5,324,315, the provision of feedback as to the proper positioning of a programming head with respect to an implanted antenna of an implanted medical device includes the use of a position indicator, for example, an audible tone generator and/or a visible indicator such as a light emitting diode (LED). When signal strength and accuracy are confirmed (e.g., with parity checking, error checking codes, and the like), programmer control circuitry will cause the position indicator to indicate that a link has been established. If adequate signal strength and content accuracy cannot be confirmed, the position indicator will so indicate.

Further, U.S. Pat. No. 5,107,833 to Barsness, entitled "Telemetry Gain Adjustment Algorithm and Signal Strength Indication in a Noisy Environment," describes provision of a signal strength indicator for providing the user with a visual alpha-numeric readout of signal strength during establishment of a telemetry link. The signal strength is derived from an automatic gain control factor of an adjustable gain amplification stage of an external communication device, e.g., the adjustable gain amplification stage of the uplink receiver of a programmer which receives its input signals from an RF programming head having an antenna configuration therein. The gain of the uplink receiver is a function of the strength of the uplink signal. As described therein, with a telemetry session initiated and uplink signal loss occurring for performing telemetry, the automatic gain control algorithms scan through gain levels searching for one which will result in valid uplink detection. A displayed range of signal strengths correspond to the scaled automatic gain control levels or factors. Since the automatic gain control value is lowest for maximum signal level and highest for minimum signal level, the value is complemented for use as a signal strength indicator to the user. As described therein, various levels of automatic gain control could be used. For example, scaled values of 0–100, or values of 0–9, may be used for display to a user attempting to position the programming head. The signal strength indicator may appear on a screen of a programmer or it could appear on the programming head as a numeric display for the user to view as the user attempts to find an optimum position for the programmer head based on the viewed strength signal indication.

Further, programmer heads available under the trade designation 9766/9766A/9767, available from Medtronic, Inc., assignee of the present invention, provide for a multiple LED array display for providing indication of proper positioning of the programmer head. The array is driven as a function of the uplink signal strength. The signal strength is determined as a function of the gain of the uplink receiver.

A certain number of LEDs of the LED array are activated based upon the signal strength. For example, when the head is not at an optimum position, only one LED may be lit. As the programmer head is moved around the site of the implanted medical device, more LEDs may be lit indicating more optimal positions. Further, no LEDs of the array may be lit until valid telemetry can be accomplished, i.e., as determined by a handshake process.

As described above, conventional RF heads incorporate various types of indicators to guide placement of the RF head. For example, the 9766 family RF he s available from Medtronic Inc., assignee of the present invention, incorporate signal strength indicator LEDs to guide placement of the RF head. Further, other positioning techniques have used numerical displays for indicating the signal strength to a user to guide placement of the RF programmer head. However, in brightly lit rooms, LEDs or visual numerical displays are sometimes difficult to see and/or read. As such, these indicators are inadequate for optimal placement of an RF programmer head.

Further, in some circumstances, implantable medical devices are implanted in various regions of the body which prohibit the viewing of an RF programmer head as it is placed over the implant site. For example, neurostimulators are sometimes implanted in the hip area. As such, when a programming head of an external communication device is placed for performing telemetry over the implant site, the user of the head may find it difficult to view LEDs on the head.

SUMMARY OF THE INVENTION

The present invention provides for the use of tactile feedback in conjunction with the positioning of a communication head for performing telemetry between an implantable medical device and an external communication device. Tactile feedback allows a user to locate an implanted device with a communication head without looking at an indicator light, a numeric display, etc.

An implantable medical device telemetry method according to the present invention includes providing an implantable medical device and an external communication device. The implantable medical device includes a device transmitter and/or a device receiver. The external communication device includes an external transmitter and/or an external receiver connected to an antenna for communication with the device transmitter and/or the device receiver. The method further includes determining validity of a communication link between the device transmitter and/or the device receiver of the implantable medical device and the external transmitter and/or the external receiver of the external communication device. Tactile indication is provided as a function of the validity determination.

In one embodiment of the method, the external communication device includes a user communication head moveable relative to the implantable medical device when the implantable medical device is implanted. The tactile indication is provided to a user via the user communication head.

In another embodiment of the method, the validity of the communication link is determined by detecting communication of a signal between the implantable medical device and the external communication device. The strength of the communicated signal is determined and the strength of the communicated signal is compared to at least one predetermined reference strength.

Further, with regard to this embodiment, a tactile indication may be provided by controlling the frequency of vibration of the tactile indication as a function of the strength of the communicated signal.

In another embodiment of the method, determining the validity of a communication link includes completing a handshake between the device transmitter and/or the device receiver of the implantable medical device and the external transmitter and/or the external receiver of the external communication device.

In yet another embodiment of the method, providing the tactile indication as a function of the validity determination may include initiation of the tactile indication upon determination of a valid communication link. Further, with regard to this particular embodiment, the tactile indication may be discontinued after a predetermined time following initiation thereof. Yet further, activation of an indicator may be provided when the valid communication link becomes invalid following such discontinuation of the tactile indication.

In yet another embodiment, the tactile indication as a function of the validity determination is provided by continuously providing tactile indication during the entire period of time that a valid communication link is determined.

Another implantable medical device telemetry method according to the present invention includes providing an implantable medical device and an external communication device. The implantable medical device includes a device transmitter and/or a device receiver. The external communication device includes a moveable head apparatus including at least an antenna therein connected to at least one of an external transmitter and/or an external receiver for communication with the device transmitter and/or the device receiver of the implantable medical device. The method further includes moving, by the user, the moveable head apparatus relative to the implantable medical device. Tactile indication is provided to the user via the moveable head apparatus upon movement of the moveable head apparatus to a position where information between the device transmitter and/or the device receiver of the implantable medical device and the external transmitter and/or external receiver of the external communication device is communicated.

An implantable medical device telemetry system is also described according to the present invention. The system includes an implantable medical device including a device transmitter and/or a device receiver and an external communication device. The external communication device includes an external receiver and/or an external transmitter connected to an antenna for communication with the device transmitter and/or the device receiver. The external communication device further includes a tactile feedback generation device and control circuitry operable to initiate the tactile feedback generation device as a function of the validity of a communication link between the implantable medical device and the external communication device.

In one embodiment of this system, the external communication device includes a user communication head moveable relative to the implantable medical device when the implantable medical device is implanted. Further, the tactile feedback generation device and the antenna of the external communication device are provided within the moveable user communication head.

In various embodiments of the system, the tactile feedback generation device may include a vibrating motor, a piezoelectric device, an electric solenoid, or a relay contact.

A communication device for establishing a communication link with an implantable medical device is also described. The device includes an external receiver and/or an external transmitter connected to an antenna for communication with a device transmitter and/or a device receiver of the implantable medical device. The communication device further includes a tactile feedback generation device and control circuitry operable to initiate the tactile feedback generation device as a function of the validity of a communication link between the implantable medical device and the external communication device.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

FIGS. 8A–8C show various illustrative embodiments of the general head positioning method illustrating tactile feedback as shown in FIG. 7.

DETAILED DESCRIPTION OF THE EMBODIMENTS

Figure 1:
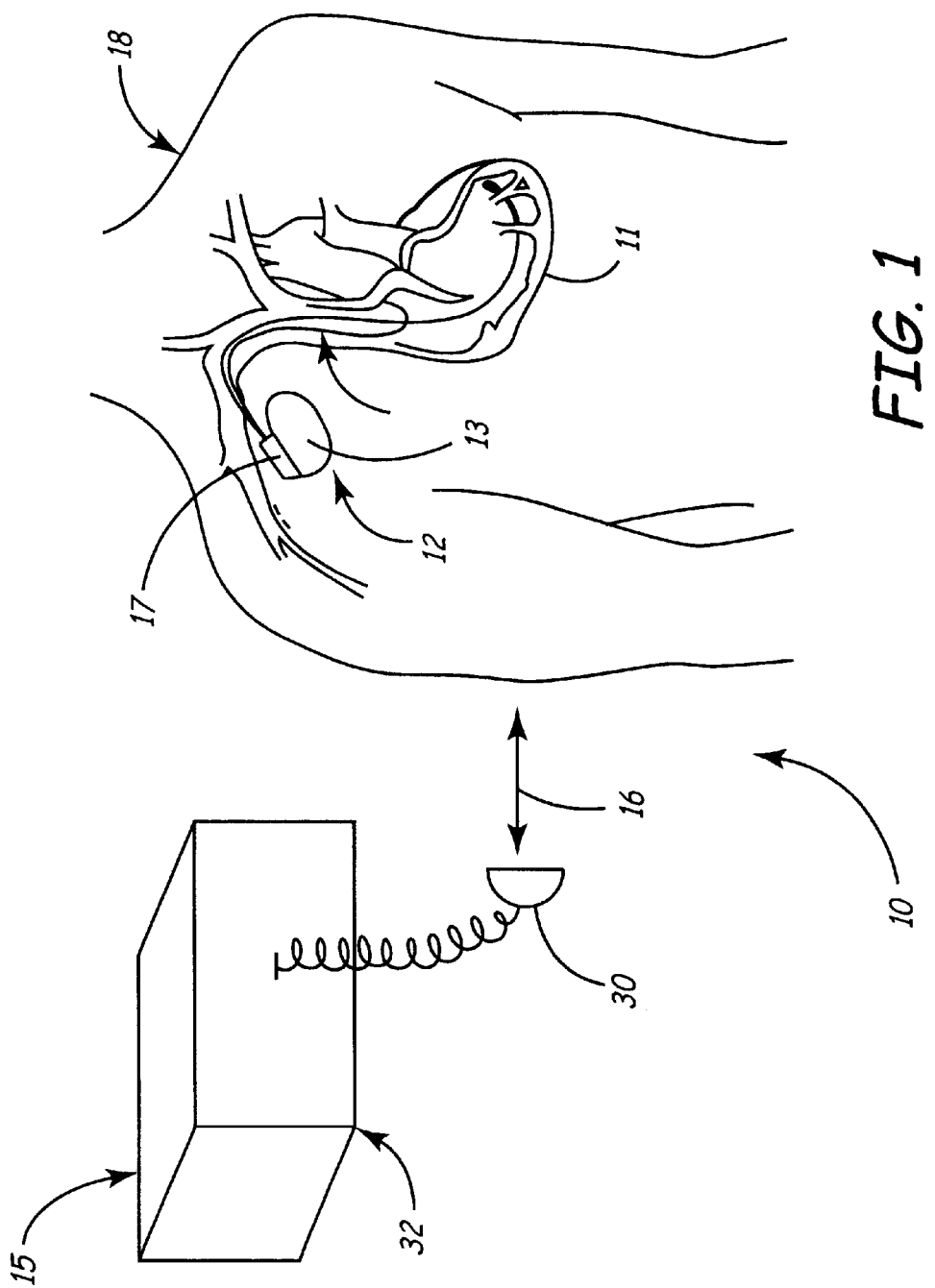
FIG. 1 is a diagram illustrating an implantable medical device in a body for communication with an external communication device, wherein the implantable medical device and external communication device provide telemetry with use of tactile feedback according to the present invention.

FIG. 1 shows a telemetry system 10 according to the present invention. The telemetry system 10 includes implantable medical device 12 and external communication device 15 which are operable for establishing a communication link 16 therebetween. Preferably, the external communication device 15 includes a controller apparatus 32, e.g., a programmer apparatus, having a communication head 30 electrically coupled thereto. The controller apparatus 32 interfaces with the implantable medical device through the use of the communication head 30, e.g., a programming head or paddle. For ease of use, the programmer head 30 is connected to other components of the programmer apparatus 32 via a cable, e.g., a straight or coiled cable, although wireless communication or any other electrical connection is possible.

Generally, the communication head 30 is a hand-held unit adapted to be placed on or in close proximity to the patient's body over the implant site of the patient's implanted medical device 12 to establish the communication link 16. Preferably, according to the present invention, the communication head 30 includes tactile feedback (also referred to herein as tactile indication) to provide a user with information as to the proper positioning of the communication head 30 relative to the implantable medical device 12.

Although the present invention is described herein with respect to tactile indication or feedback being provided via the hand-held communication head 30, such tactile indication may be provided to the user by any other suitable apparatus. For example, the tactile feedback may be provided via a device located proximate another portion of the user's body such as a wearable wristband, an apparatus attachable to a user's pocket or other portions of clothing, or any other apparatus capable of providing tactile indication to the user. As used herein, tactile indication or tactile feedback refers to any feedback perceivable by a user's sense of touch, e.g., vibratory motion transmitted to the housing of the communication head 30 and therefore to a user's hand holding the hand-held communication head 30, or any other motion perceivable by the user's sense of touch.

Figure 2:
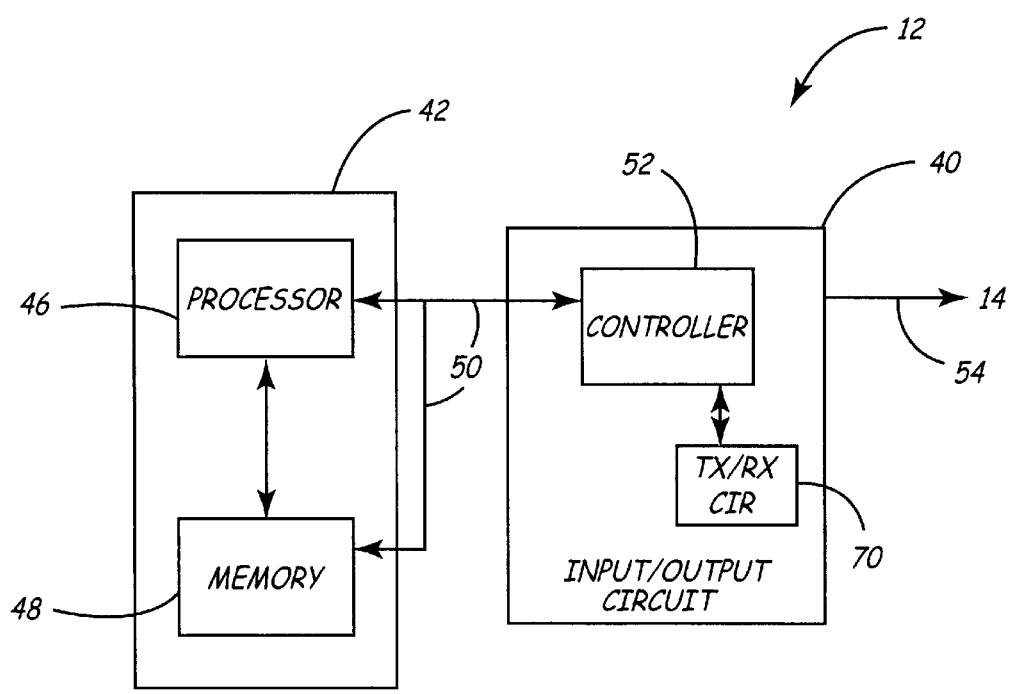
FIG. 2 is a general block diagram of circuitry of an implantable medical device including transmitter and receiver circuitry according to the present invention.
Figure 3:
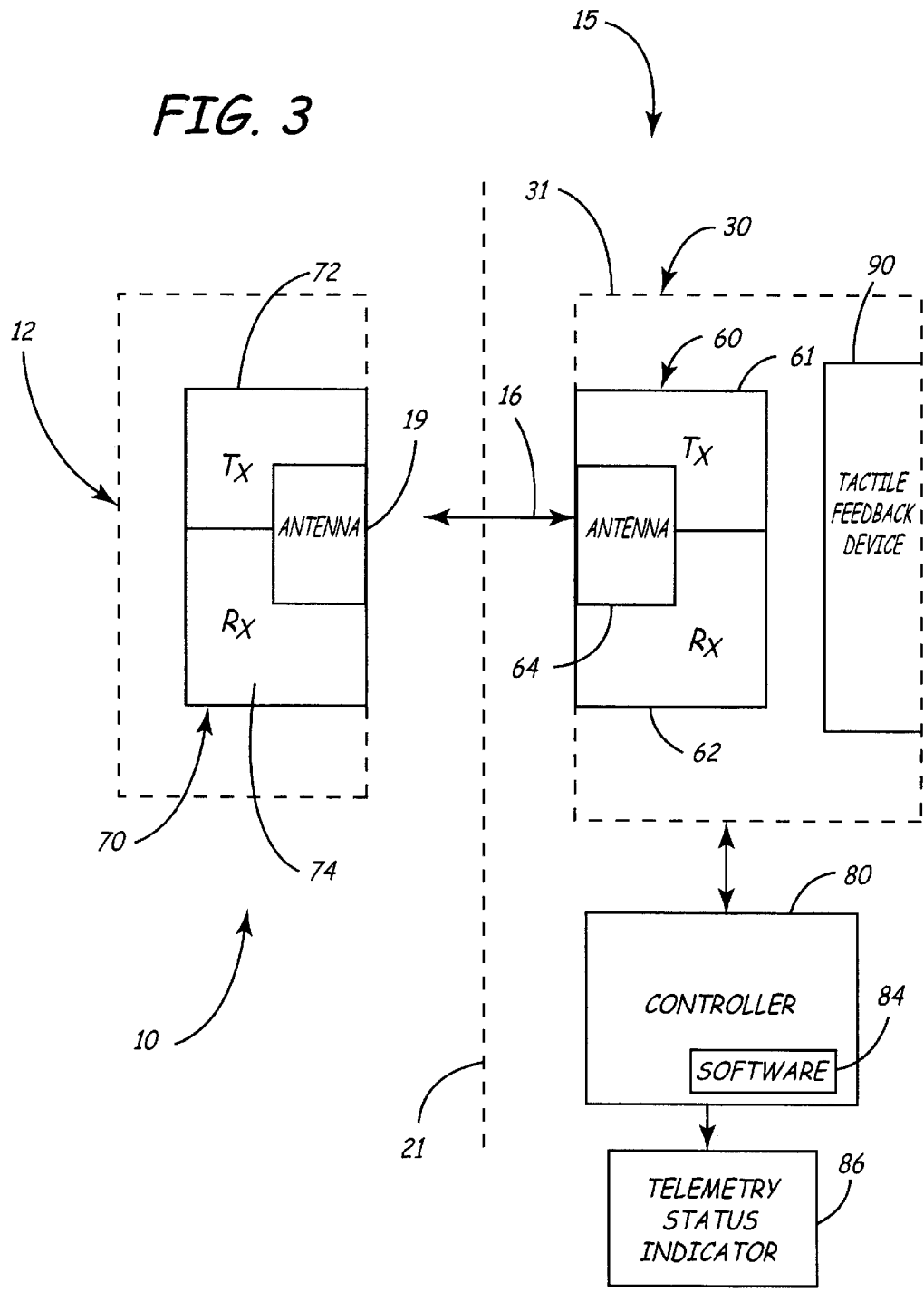
FIG. 3 is a general block diagram of an illustrative telemetry system using tactile feedback according to the present invention.

As shown in FIG. 1, implantable medical device 12 is implanted in body 18. Implanted device 12 includes a housing 13 in which components of the implantable medical device 12 are hermetically sealed, e.g., pacing circuitry, defibrillation circuitry, a battery, monitoring circuitry, etc. Also positioned within the housing 13 is transmitter/receiver circuitry 70, as shown in FIGS. 2 and 3. As illustratively shown in FIG. 1, at least one lead 14 is connected to the illustrative implantable medical device 12 in connector block region 17 such as with the use of feedthrough(s) (not shown). For example, the implantable medical device 12 may be implanted near a human heart 11. In the case where the implantable medical device 12 is an illustrative pacemaker implanted in the body 18, the pacemaker may include a pacing and sensing lead represented generally as lead 14 to sense electrical signals attendant to the depolarization and repolarization of the heart 11, and to provide pacing pulses for causing depolarization of cardiac tissue in the vicinity of the distal ends thereof.

Implantable medical device 12 may be any implantable medical device embodying transmitter/receiver circuitry as described herein. For example, in the case where the implantable medical device is a pacemaker, the implantable device may be, for example, a pacemaker such as that described in U.S. Pat. No. 5,158,078 to Bennett, et al.; U.S. Pat. No. 5,312,453 to Shelton et al.; or U.S. Pat. No. 5,144,949 to Olson et al.

Implantable medical device 12 may also be a pacemaker-cardio-verter-defibrillator (PCD) corresponding to any of the various commercially-available implantable PCDs. For example, the present invention may be practiced in conjunction with PCDs such as those described in U.S. Pat. No. 5,545,186 to Olson, et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker, et al.

Alternatively, implantable medical device 12 may be an implantable neurostimulator or muscle stimulator such as that disclosed in U.S. Pat. No. 5,199,428 to Obel, et al.; U.S. Pat. No. 5,207,218 to Carpentier, et al.; or U.S. Pat. No. 5,330,507 to Schwartz, or an implantable monitoring device such as that disclosed in U.S. Pat. No. 5,331,966 to Bennett, et al.

Further, for example, the implanted device 12 may be a cardioverter-defibrillator, a brain stimulator, a gastric stimulator, a drug delivery device, a hemodynamic monitoring device, or any other implantable device that would benefit from telemetry capabilities according to the present invention using tactile feedback. Therefore, the present invention is believed to find wide application. As such, the description herein making reference to any particular medical device is not to be taken as a limitation of the type of medical device which may be used in association with the tactile feedback of external communication device 15 according to the present invention.

FIG. 2 generally illustrates a high level block diagram of constituent components of one embodiment of implantable medical device 12, where the medical device is implemented with a microprocessor-based architecture. However, the electronic features and operations of the implantable medical device 12 may be implemented in discrete logic or as a microcomputer-based system. As shown in FIG. 2, the implantable medical device 12 includes a microcomputer circuit 42 including at least a processor 46 and memory 48. The microcomputer circuit 42 is coupled by a data communication bus 50 to a controller circuit 52 of an input/output circuit 40. For example, microcomputer circuit 42 may form a custom integrated circuit device augmented by standard RAM/ROM components.

Further, for example, the input/output circuit 40 may include any other number of circuits in addition to the controller 52 such as is necessary for accomplishing the function of the implantable medical device 12. For example, the input/output circuit 40 may include sense amplifiers, peak sense and threshold measurement units, bias circuits, pulse generators, threshold detectors, etc., along with other input/output circuits such as those required to provide the controller 52 with appropriate signaling information. The specific embodiments of such circuits are not critical to the practice of the present invention so long as the circuits provide for generating signals corresponding to the desired implantable medical device and/or are capable of providing controller 52 with signals indicative of applicable physiological events, e.g., natural and stimulated contractions of the heart, and also so long as the implantable medical device 12 includes transmitter/receiver circuitry 70 according to the present invention for use in a telemetry system 10 as described herein.

FIG. 3 is a block diagram of the telemetry system 10 including the implantable medical device 12 such as described above with reference to FIG. 2 and the external communication device 15. A dashed line 21 represents the boundary (e.g., the patient's skin) between the implanted medical device 12 and external communication device 15.

As described above, the implantable medical device 12 includes at least transmitter/receiver circuitry 70 for establishing a communication link with external communication device 15. Transmitter/receiver circuitry 70, including transmitter circuit 72 and receiver circuitry 70, is coupled to antenna 19. Although the transmitter/receiver circuitry 70 is shown to include only transmitter circuit 72 and receiver circuit 74, other circuitry for controlling such transmitter and receiver circuits 72, 74 also form a part of implantable medical device 12, e.g., processors for controlling wake-up functions, controlling flow of data to the transmitter for modulation on a carrier signal, etc. In addition, other components of the implantable device 12, e.g., battery, provide power to such circuitry. The antenna 19 may be of any antenna type utilized in implantable medical device applications for telemetry functions, e.g., multi-turn wire coil antennas.

The transmitter/receiver circuitry 70 generates modulated electrical signals for provision to an antenna 19 such that electromagnetic waves are radiated. An antenna 64 associated with the communication head 30 receives the electromagnetic waves from the implanted medical device 12. Transmitter/receiver circuitry 60 of the external communication device 15 receives and demodulates the modulated electrical signals induced in the antenna 64 representative of the electromagnetic waves radiated from the antenna 19 of the implantable medical device 12.

Generally, the external communication device 15 is an apparatus having at least transmitter/receiver circuitry 60 and an antenna 64 for transmitting and receiving electromagnetic energy. Further, the external communication device 15 includes control circuitry 80 (e.g., processor, software 84, memory, etc.) connected for control of telemetry transceiver circuitry 60. The external communication device 15 may be any programmer such as those used in telemetry systems for receiving information from an implantable medical device 12 and transmitting information thereto. Generally, as previously described herein, such programmers are used to adjust parameters of implantable medical devices and typically have graphic displays, keyboards, or other user interfaces for data entry and device control by operator manipulation. Further, such programmers generally include printers or plotters to allow the user to control, evaluate, and document the extensive capabilities of implanted device 12 from which it is receiving information.

For example, external communication device 15 may include various devices available from Medtronic, Inc., assignee of the present invention. For example, such devices may include programmers operable with communication heads available from Medtronic, Inc. such as a 9790 programmer operable in conjunction with RF heads including those available from Medtronic, Inc. under the trade designation 9766 RF Heads, 9766A RF Heads, and 9767 RF Heads; and a Medtronic 2090 programmer which is operable with a 9767 RF Head. Further, the devices 15 may include patient activators, e.g., patient activated devices for freezing memory recordings, such as a Medtronic 9462 patient activator; Medtronic 9464 patient activator; or a Medtronic 6190 or 6191 patient activator. Yet further, the device 15 may be a neurostimulator programmer such as those available under the trade designation Medtronic 7432 programmer, Medtronic 3425 programmer, Medtronic 3210 programmer; or a drug delivery device programmer available under the trade designation Medtronic 8820 programmer which is operable with a 9766 RF head. Each of such devices may be modified according to the present invention to provide tactile feedback to a user when attempting to establish a communication link between the implantable medical device 12 and the external communication device 15.

The transmitter/receiver circuitry 60 of external communication device 15 generates modulated electrical signals for provision to antenna 64 of the communication head 30 such that electromagnetic waves are radiated. The antenna 19 associated with the implantable medical device 12 receives, the electromagnetic waves from the external communication device 15. The transmitter/receiver circuitry 70 of the implantable medical device 12 receives and demodulates the modulated electrical signals induced in the antenna 19 representative of the electromagnetic waves radiated from the antenna 64 of the external communication device 15.

As would be known to one skilled in the art, the transceiver circuitry 60 of the external communication device 15 includes receiver circuitry 62 that is compatible with the transmitter 72 of the implanted medical device 12 and operable for receiving and demodulating the transmitted signal therefrom. Further, the transceiver circuitry 60 of external communication device 15 includes transmitter circuitry 61 that is compatible with the receiver 74 of the implanted device 12 and operable for generating a modulated signal of which the receiver of the implanted medical device 12 is capable of receiving and demodulating. The transceiver circuitry 60 is coupled to antenna configuration 64 for communicating with the implantable medical device 12 via antenna 19.

Antenna 64 is preferably disposed within hand-held communication head 30 surrounded by a housing 31 generally represented by dashed line in FIG. 3. The hand-held communication head 30 can then be conveniently placed in proximity to the patient's implant site. When so positioned, antenna 64 receives uplink telemetry signals transmitted from implanted medical device antenna 19 and transmits downlink telemetry signals to be received by implanted medical device antenna 19 as indicated by the double-arrowed communication link 16.

It will be readily apparent to one skilled in the art from the description herein that the present invention need not be used as a bi-directional telemetry system, but may be used as a unidirectional system. In other words, external communication device 15 may only include a receiver to receive information from a transmitter of implantable medical device 12. For example, this may be the case in an implantable monitoring device. Likewise, external communication device 15 may only include a transmitter for transmitting information to a receiver of the implantable medical device 12. This may be the case where implantable medical device 12 is only being programmed by the external communication device 15.

To provide feedback as to the proper positioning of the communication head 30 relative to the implanted medical device antenna 19 to establish a valid communication link, tactile feedback generation device 90 is provided according to the present invention. Unlike conventional indicator devices, tactile feedback generation device 90 allows a user to locate an implantable medical device 12 using the communication head 30 without the requirement of looking at an indicator light. However, as further described below, other indicators may be used in conjunction with the tactile feedback generation device 90. For example, a position indicator or telemetry status indicator 86 may be used in conjunction with the tactile feedback to properly position the external antenna 64 relative to the implanted medical device antenna 19, e.g., the telemetry status indicator may be activated after a handshake is performed and confirmation thereof is attained indicating that at a valid communication link has been established at a certain communication head position, while tactile feedback may be used to indicate a more optimal position for the communication head 30.

Figure 7:
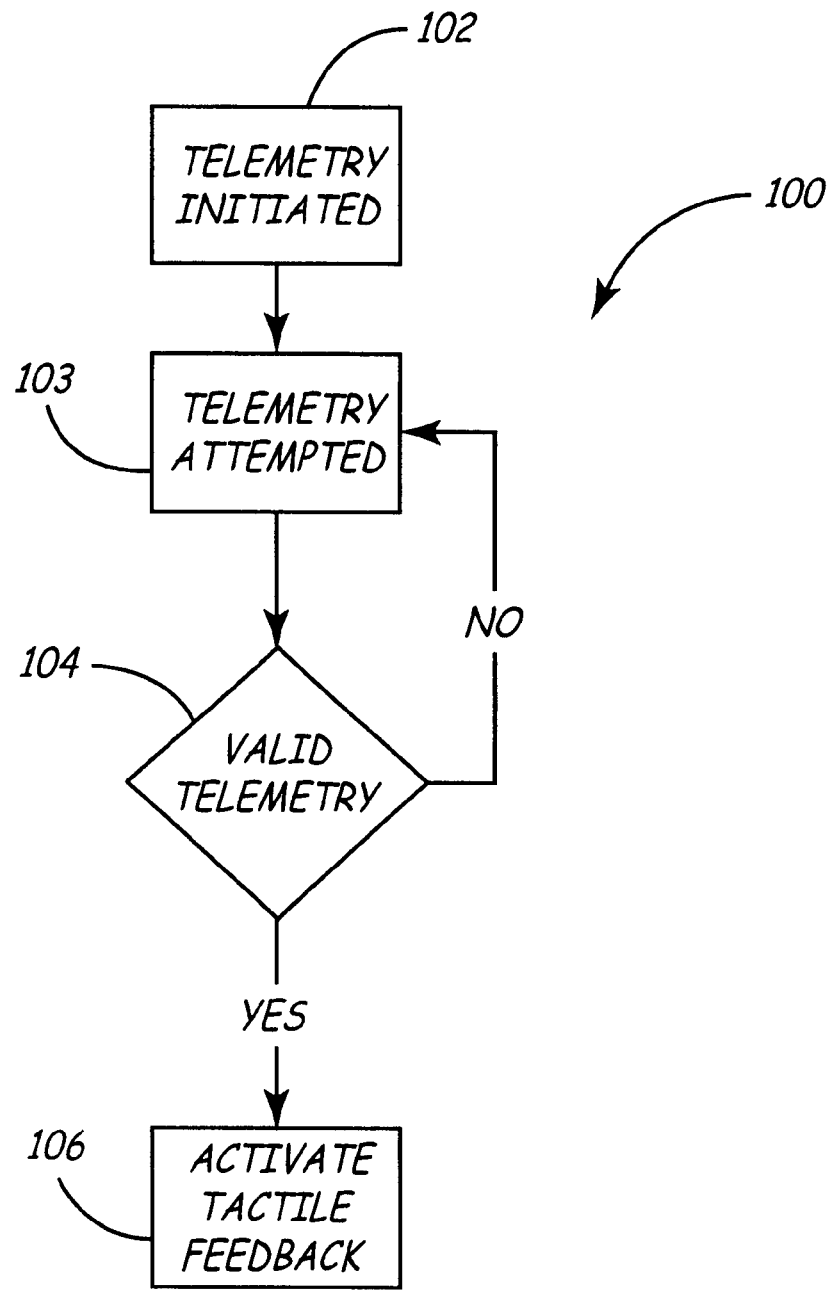
FIG. 7 is a general block diagram of a head positioning method illustrating tactile feedback according to the present invention.

The use of tactile feedback in positioning the communication head 30 for performing telemetry according to the present invention shall be first generally described with reference to the general head positioning method 100 of FIG. 7 and then various illustrative embodiments of such a general method shall be described with reference to FIGS. 8A–8C. Head positioning method 100 generally includes the initiation of a telemetry session as shown in block 102. For example, a telemetry session may be initiated by the closing of a reed switch of an implantable medical device 12 as is known in the art, may be initiated by a wake-up pulse, or may be initiated by any other technique for beginning a telemetry session. Thereafter, telemetry is attempted (block 103) under control of control circuitry 80. It is then determined whether valid telemetry has been accomplished (block 104) or, in other words, whether a valid communication channel or link is established between the implantable medical device 12 and the external communication device 15. If such a valid telemetry link is not determined, then no tactile feedback is provided to the user. As such, the user knows that the user communication head 30 must be moved relative to the implanted device 12 Further communication between the implantable medical device 12 and the external communication device 15 is then attempted with the communication head 30 in a new position. Once valid telemetry is achieved, tactile feedback is activated (block 106) based on the telemetry validity determination (block 104).

One skilled in the art will readily recognize that various techniques may be used for determining valid telemetry (block 104). For example, valid uplink telemetry may be determined, valid downlink telemetry may be determined, bi-directional valid telemetry may be determined, signal strength may be used for determining valid telemetry, handshaking may be used to determine valid telemetry, CRC checking or error checking may be used to determine valid telemetry, or any other processes or combination of processes for determining that a channel is valid may be used according to the present invention.

Further, one skilled in the art will recognize that tactile feedback may be used in different manners to indicate valid telemetry under is different circumstances or different applications. For example, tactile feedback may be used upon initial detection of a valid communication channel even though the communication head may not be at a position that provides a signal of optimum strength; tactile feedback may be used only upon finding a communication head position that provides a telemetry signal of a particular strength as determined by a predetermined reference strength level; tactile feedback may be used to indicate an initial detection of a valid communication channel with the tactile feedback being modified as a function of signal strength as positions providing greater or lesser signal strength are located; etc.

Figure 8A:
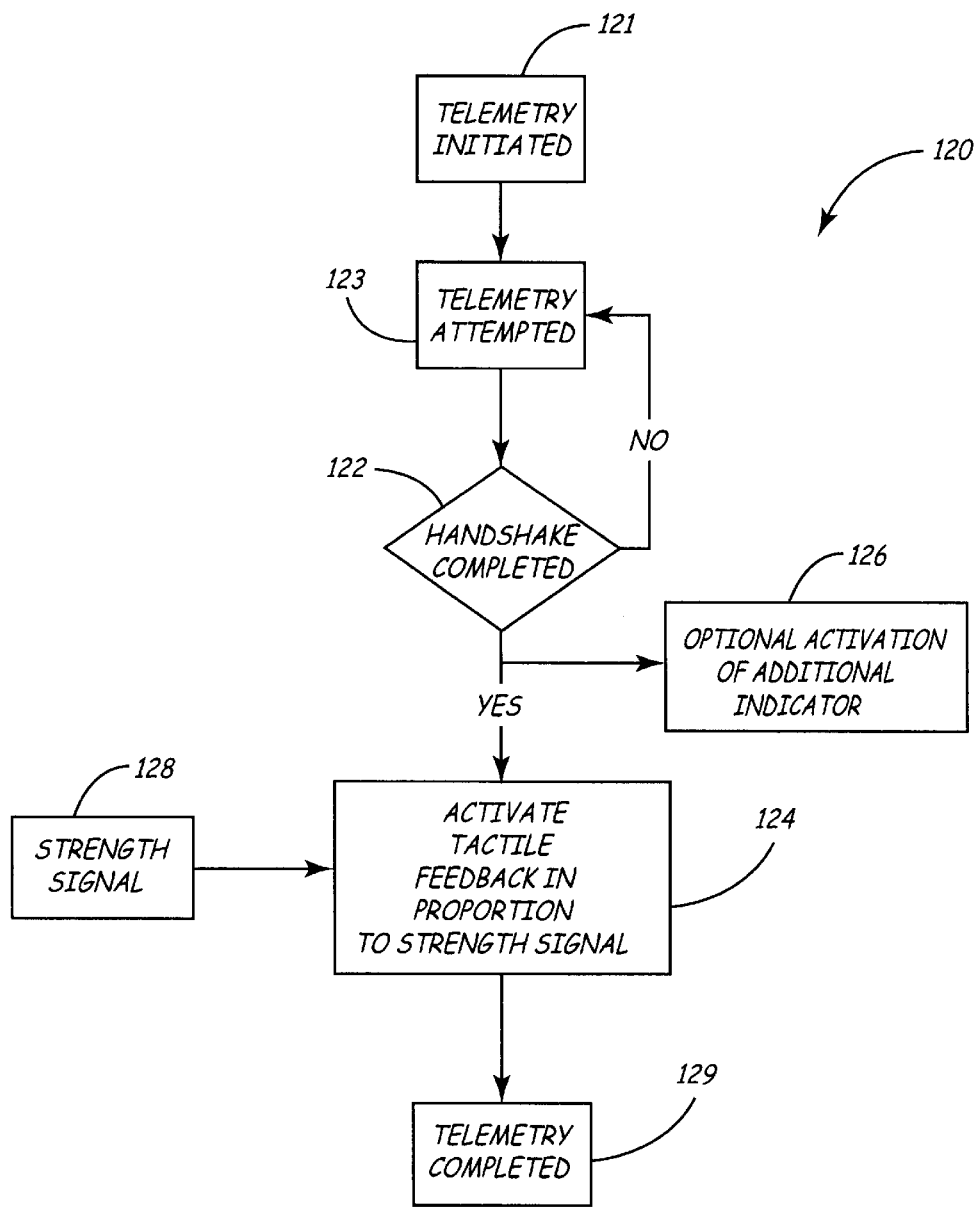
Figure 8C:
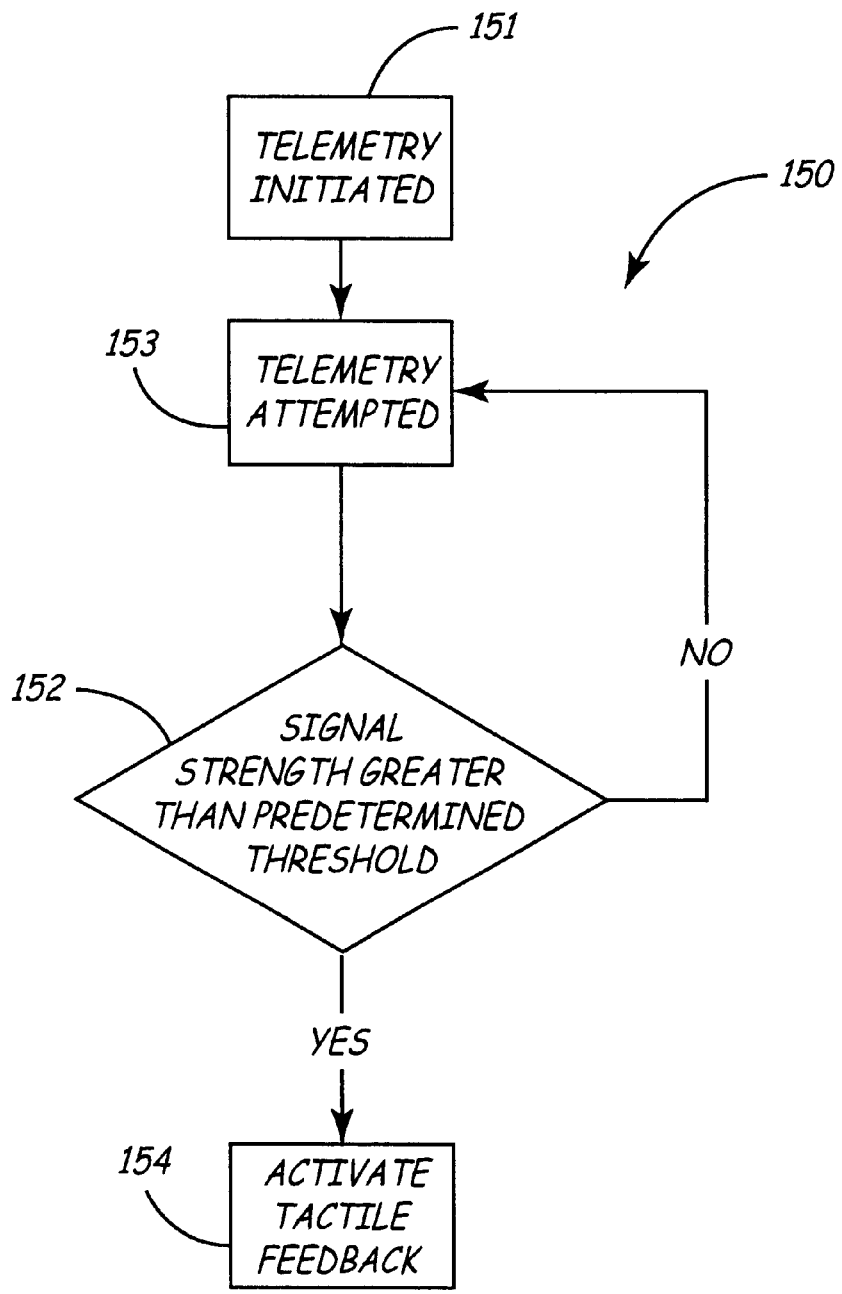

FIGS. 8A–8C are provided to illustrate several embodiments of the general head positioning method 100 described above with reference to FIG. 7. As shown in FIG. 8A, head positioning method 120 includes telemetry initiation (block 121). For example, as described above, a telemetry session may be initiated by the closing of a reed switch of an implantable medical device 12 as is known in the art, may be initiated by a wake-up pulse, or may be initiated by any other technique for beginning a telemetry session. Thereafter, telemetry is attempted (block 123) such as by starting a handshake protocol. For example, after initiation of the telemetry session (block 121), a handshake sequence may be periodically performed to establish and/or continually assess a valid telemetry link.

Generally, the handshake protocol includes carrying out a handshake sequence that includes a handshake request, a window of time for a response to the request, and a handshake confirmation. One skilled in the art will recognize that either the implantable medical device 12 or the external communication device 15 may be used to initiate the handshake sequence with a handshake request. Preferably, the handshake sequences are initiated by a handshake request from the implantable medical device 12. For example, the handshake protocol may be performed in a manner such as that described in U.S. Pat. No. 5,292,343 to Blanchette, et al., entitled "Handshake for Implanted Medical Device Telemetry."

Figure 9:
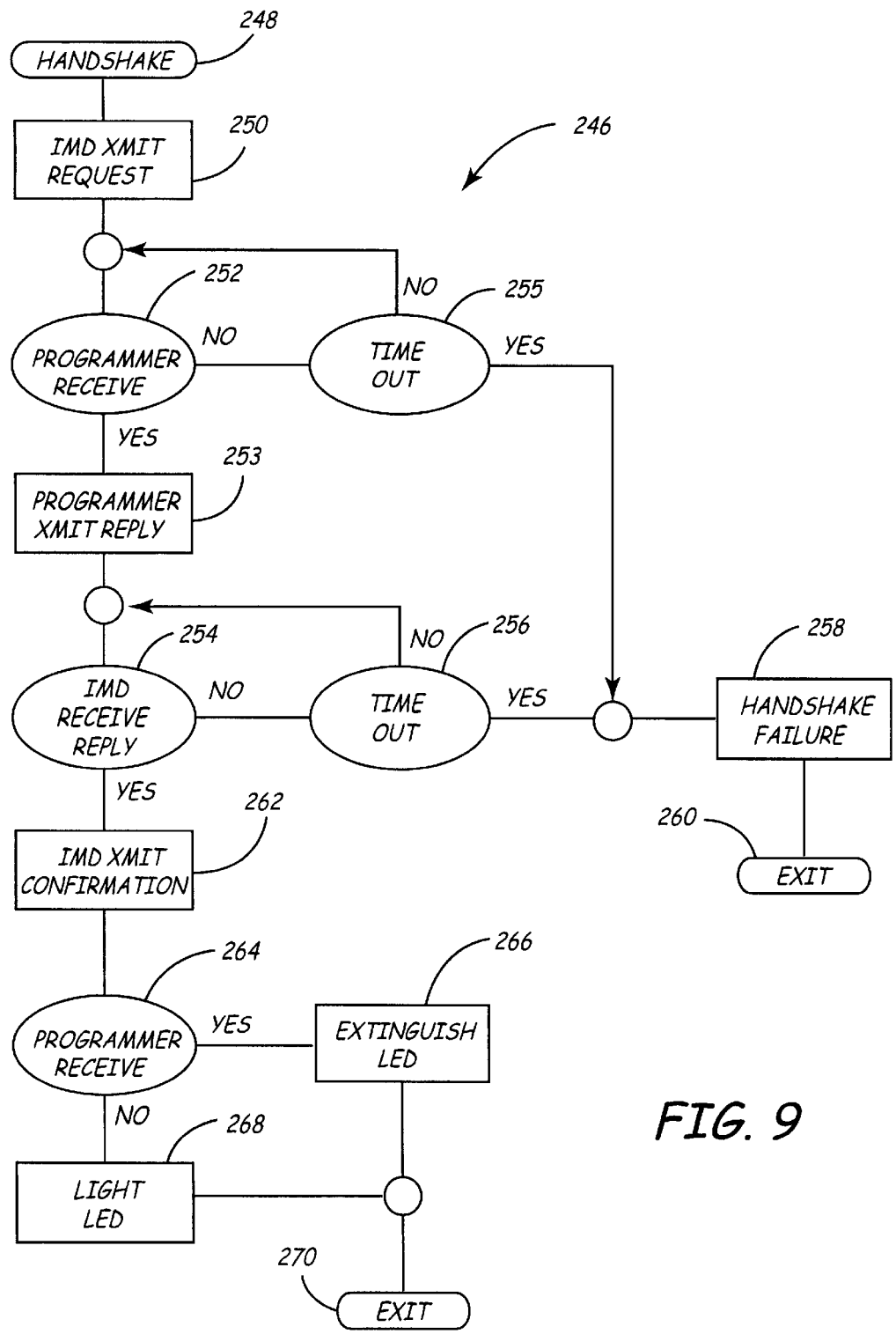
FIG. 9 is a block diagram of one illustrative embodiment of a handshake used according to the present invention for determining validity of a communication link.

FIG. 9 shows one illustrative embodiment of a handshake procedure 246 which may be used in conjunction with the telemetry system 10. One skilled in the art will recognize that various handshake sequences and techniques may be used to determine a valid communication channel between the implantable medical device 12 and the external communication device 15. As such, the present invention is not limited to any particular handshake sequence or technique. It will be further recognized that handshake sequences are periodically carried out during an initiated telemetry session to determine that a link is still valid as well as at the beginning of a telemetry session to determine the establishment of a valid communication channel.

As shown in FIG. 9, the illustrative handshake procedure 246 is initiated at handshake block 148. The implantable medical device 12 transmits the handshake request (block 250). If the external communication device 15, e.g., programmer, receives the handshake request as determined at block 252, then external communication device 15 (e.g., programmer) transmits a handshake reply (block 253) during a handshake reply window. If the programmer 15 does not receive the handshake request, a time-out period is issued so as to continue waiting for the handshake request (block 255). If, during the time-out, external communication device 15 receives a handshake request, a handshake reply (block 253) is issued. Block 256 illustrates that some time during the time-out is expended by the implanted medical device 12 in waiting for the handshake reply. If during the time-out no handshake reply is received by the implanted medical device 12 indicating that the handshake request was not received by external communication device 15, a handshake failure (block 258) is issued and the handshake sequence is exited (block 260) until the next periodic handshake sequence. A properly timed reply during the reply window from the external communication device 15 received by the implantable medical device 12 (block 254) causes transmission of a handshake confirmation (block 262).

As shown in FIG. 8A, upon completion of the handshake sequence, if a confirmation was not received, then further communication is attempted, e.g., another handshake is attempted (block 123). On the other hand, if the handshake is confirmed (block 122), then optionally, a visual or audible indicator is provided (block 126) and, according to the present invention, tactile feedback may be also activated (block 124). The optional indication shown by block 126 in FIG. 8A is also illustrated in FIG. 9. For example, as shown in FIG. 9, upon receipt of the confirmation (block 264) by the external communication device 15, an indication that a link is established may be provided, e.g., an LED is extinguished (block 266). Likewise, an indication that the confirmation was not received may also be indicated in some manner, e.g., an LED is lighted (block 268). Thereafter, the handshake sequence is exited (block 270).

Although tactile feedback may be provided in response to a confirmed handshake as described above which indicates a valid communication channel to the user, tactile feedback may be inhibited until a determination has been made that the telemetry signal strength meets a predetermined reference level. This determination is further described below with reference to FIG. 8B.

Further, as shown in FIG. 8A, in addition to the activation of tactile feedback upon confirmation of a valid handshake, the tactile feedback may be adjusted as a function of the telemetry signal strength (block 124). The signal strength (block 128) is provided such that the tactile feedback may be activated as a function thereof. For example, the frequency of vibration may be increased as signal strength (block 128) is increased. Likewise, the frequency of vibration of the tactile feedback may be decreased upon a decrease in signal strength (block 128). In such a manner, the user is provided with a varied tactile feedback as a function of the signal strength such that optimum positioning of the head 30 can be attained by the user. For example, the user may move the handheld communication head 30 to the position where tactile feedback having the high frequency of vibration is sensed. With the communication head 30 properly positioned, telemetry is completed (block 129).

Signal strength may be determined by any number of different techniques. Such signal strength may be representative of uplink signal strength, downlink signal strength, or a combination of uplink and downlink signal strength. For example, when uplink telemetry signals are received by antenna 64 and uplink receiver 62, the strength of the received signals can be assessed or monitored based upon the gain setting of the uplink receiver 62. Such monitoring of the gain is, for example, described in U.S. Pat. No. 5,107,833 to Barsness and U.S. Pat. No. 5,324,315 to Grevious. Generally, the gain of the uplink receiver 62 is inversely proportional to the signal strength. For example, a lesser signal strength results in a higher gain being provided by the receiver 62, and a higher signal strength results in a lesser gain being provided by receiver 62.

FIG. 8B illustrates another alternate embodiment of a head positioning method 130. The head positioning method 130 includes initiating telemetry (block 131) in a like manner as described with reference to FIG. 8A. Likewise, as shown in block 133, telemetry is attempted and a handshake sequence 132 is performed. Upon confirmation of the handshake (block 132), a telemetry status indication may be optionally provided to the user (block 135), e.g., telemetry status indicator 86 as shown in FIG. 3 is activated.

Thereafter, upon confirmation of the handshake (block 132), signal strength (provided as described previously with reference to FIG. 8A) based on gain of the uplink receiver 62 is compared to a reference threshold. Such a comparison may be accomplished in any number of manners, and is not limited to any particular comparison circuit. If such a reference threshold is not met, then the user is not provided with tactile feedback and the user recognizes the need to change the position of the communication head 30. Further attempts to perform telemetry are then carried out (block 133). However, if the telemetry signal strength satisfies, e.g., is greater than, the reference threshold (block 134), then tactile feedback is activated (block 136) indicating to the user that a valid communication channel is established.

Thereafter, optionally, according to this embodiment, the tactile feedback may be deactivated (block 138) after a predetermined time even though a valid communication channel still exists between the implantable medical device 12 and the external communication device 15, i.e., the telemetry signal strength satisfies the reference threshold requirements. However, as described previously, handshake sequences are still carried out periodically and continuously evaluate whether the link continues to be valid over time. If a handshake sequence is not confirmed after the tactile feedback has been deactivated (block 138), the communication link is no longer valid (block 140) and an alarm indicator (block 144) is activated to indicate to the user that the user must reposition the communication head 30 (block 146) such that a valid communication link can be re-established. If, however, continual confirmation of the handshakes are completed, the user understands that the link is still valid and communication continues until telemetry is completed (block 142).

Another illustrative alternate embodiment of a head positioning method 150 is shown in FIG. 8C. In this embodiment, after a telemetry session is initiated (block 151), telemetry is attempted (block 153). However, in this particular embodiment the signal strength based on the gain of the uplink receiver 62 is compared to a predetermined threshold reference (block 152). If the signal strength is greater than the predetermined threshold reference, then tactile feedback is activated (block 154) and the valid telemetry can be performed. However, if the signal strength is not greater than the predetermined threshold, then the user must move the communication head 30 to another position relative to the implanted medical device 12 such that further telemetry may be attempted (block 153) and further comparisons of signal strength to a threshold can be carried out until the signal strength is great enough to activate tactile feedback (block 154) such that the user knows that a valid communication channel is established between the implantable medical device 12 and external communication device 15.

One skilled in the art will recognize that the implementation of providing tactile feedback to a user may be performed under the control of software 84 of control circuitry 80 of the external communication device 50 as shown in FIG. 3. As such, various techniques of using the tactile feedback can be implemented, including but clearly not limited to controlling when tactile feedback is provided to a user based on any number of factors such as signal strength, error detection, cyclic redundancy checking, handshake confirmation, etc. For example, the determination of a valid channel using a handshake sequence may be used alone or in combination with the use of signal strength to initiate tactile feedback, and signal strength may be used alone to determine the validity of the channel as compared to use of a handshake sequence.

Further, one skilled in the art will recognize that these illustrative embodiments of determining the validity of the communication channel between the implanted medical device 12 and the external communication device 15 are given for illustration only and that there are various other methods which may be used to determine a valid communication channel. The present invention is not limited to any particular validity determination method but is limited only to the use of tactile feedback to assist the user in positioning the communication head 30 relative to the implanted medical device 12 such that when a valid communication channel has been determined the user is effectively notified.

Figure 4:
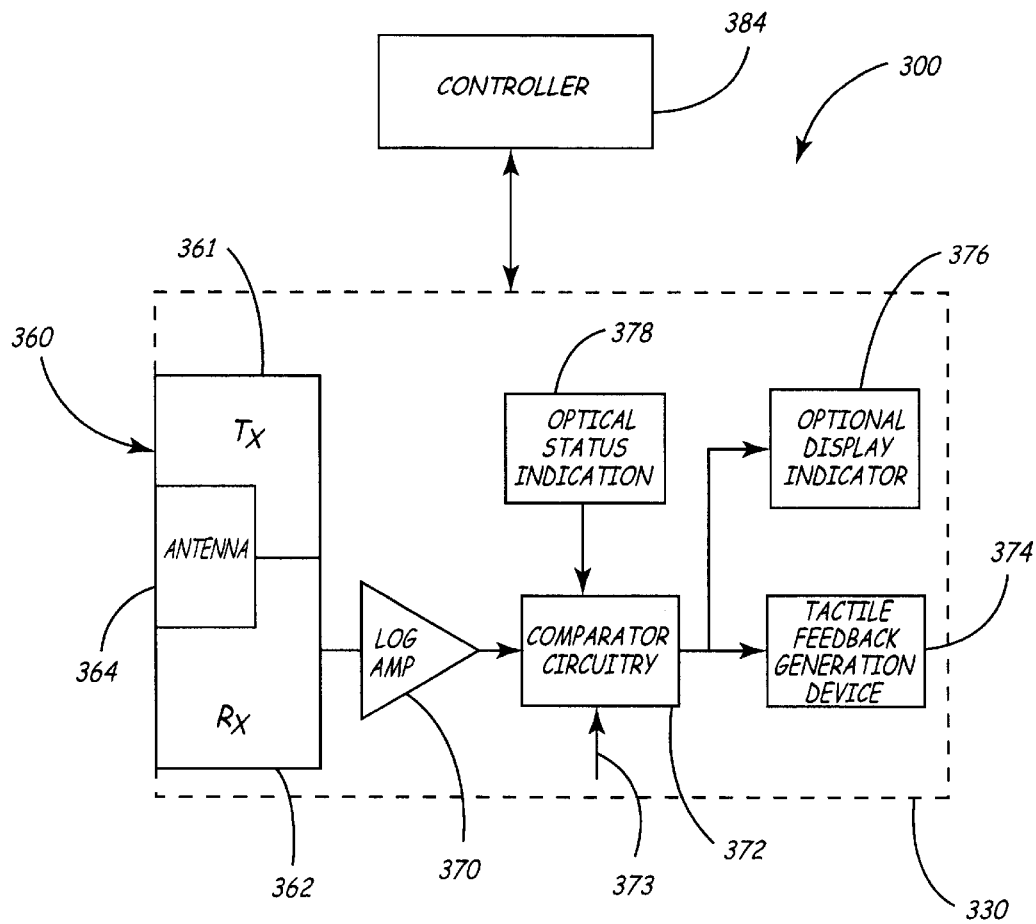
FIG. 4 is one embodiment of a portion of the illustrative external communication device shown generally in FIG. 3 according to the present invention.

A more detailed diagram of one illustrative embodiment of a portion of an external communication device 300 for carrying out tactile feedback for positioning of a communication head according to the present invention is shown in FIG. 4. The external communication device 300 includes communication head 330 electrically connected to control circuitry 384. The communication head 330 includes therein an antenna 364 coupled to transceiver circuitry 360 including downlink transmitter 361 and uplink receiver 362. Generally, the uplink receiver 362 includes an automatic gain control amplification stage (not shown) which provides for adjustment in gain based on signal strength, e.g., uplink and/or downlink signal strength. A signal representative of the gain is provided to a log amplifier 370 which provides as an output thereof a signal representative of the log of the signal strength. The log of the signal strength is compared to a reference strength 373 as generally illustrated by comparator circuitry 372. The tactile feedback generation device 374 is controlled by comparator circuitry 372. The comparator circuitry 372 has applied thereto a threshold reference 373 which is used for the comparison to the output of log amplifier 370 representative of the gain of uplink receiver 362, and has applied thereto an optional status indication 378.

Optional status indication 378 is controlled via controller circuitry 384 which is also used in controlling the handshake between the external communication device 300 and an implantable medical device 12. When valid telemetry is detected per the handshake, optional status indication 378, e.g., an LED, may be used to indicate to the user that a telemetry channel has been validated. Further, an enable signal is provided to the comparator circuitry 373 upon occurrence of a confirmed handshake such that only if the handshake is confirmed can tactile feedback be performed. As such, even if the handshake is confirmed, it is not certain that the placement of the communication head 330 is optimum for the telemetry link. Therefore, the log of the strength signal output from log amplifier 370 is provided to comparator circuitry 372 for comparison to a threshold level 373. In this embodiment, only upon the strength signal meeting the threshold reference 373 is tactile feedback device 374 activated.

It will be recognized that various threshold levels may be used for comparison with the output of the log amplifier 370 such that various optional indication devices 376 may be activated. For example, and as further described below with reference to FIG. 5, an array of LEDs may be used to visually indicate to a user the strength of the telemetry signal. Likewise, the tactile feedback generation device 374 may be controlled by the strength signal, e.g., the frequency of vibration of the tactile feedback generation device 374 may be varied according to the strength of the telemetry signal.

Figure 5:
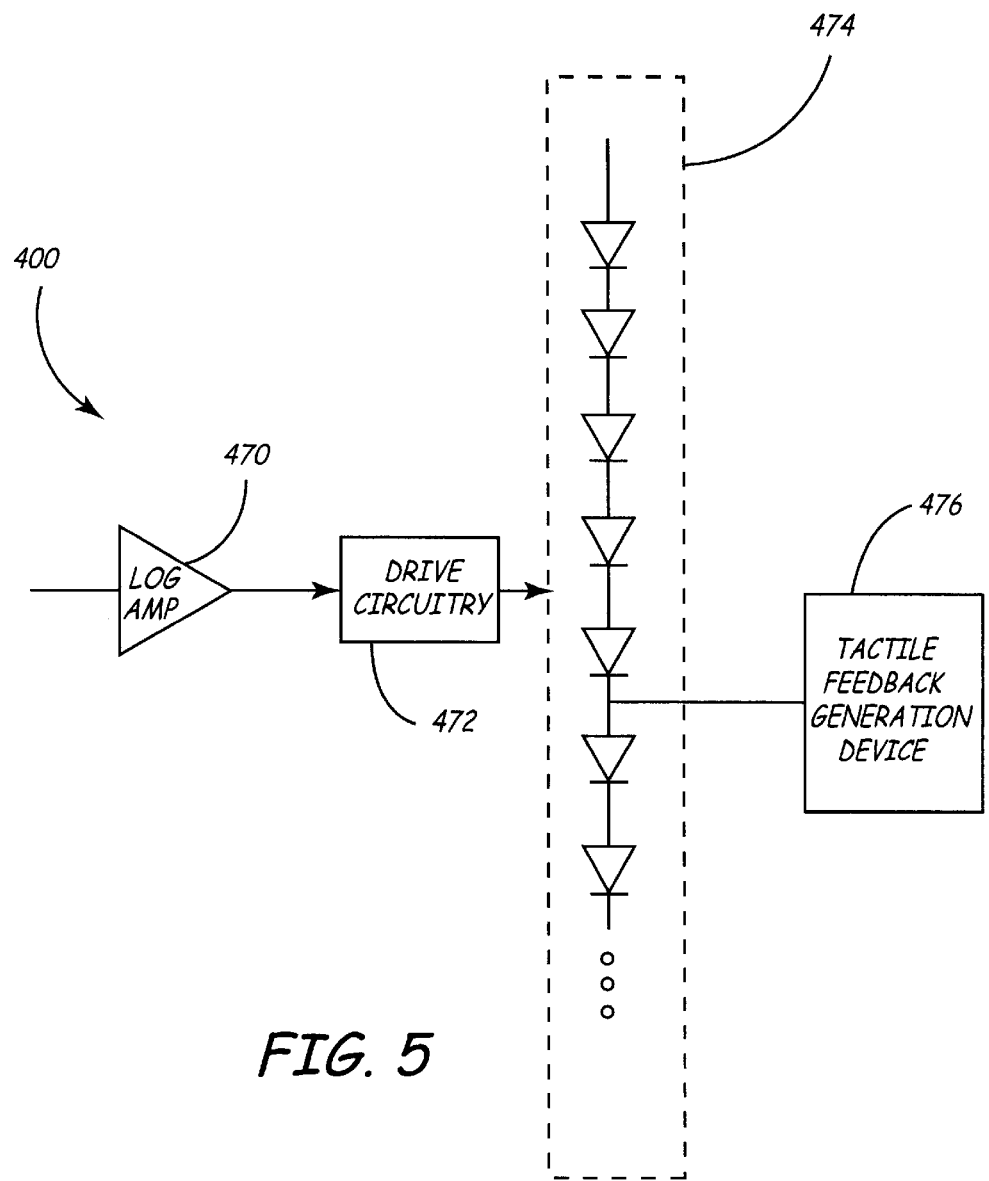
FIG. 5 is a more detailed diagram of one illustrative embodiment of a portion of the external communication device shown in FIG. 4 according to the present invention.

FIG. 5 shows one illustrative embodiment of a portion of an external communication device 400 similar to that of FIG. 4 showing the use of an array of LEDs 474 in combination with tactile feedback. As shown therein, the log amplifier 470 receives as its input a signal representative of the gain of the uplink receiver and provides an output representative of the log of the signal strength to driver circuitry 472. Driver circuitry 472 is configured to drive an array of LEDs 474 as a function of the signal representative of the log of the signal strength output from the log amplifier 470. For example, with a lower strength signal, only a single LED of the array 474 may be lit while as the strength signal is increased, more LEDs may be lit.

As further shown in FIG. 5, tactile feedback generation device 476 may be coupled to any point of the LED array such that tactile feedback may be provided to the user by the generation device 476 upon activation of a certain number of LEDs of the array 474. For example, it may be desired that tactile feedback be provided to the user upon illumination of three LEDs corresponding a certain signal strength.

Figure 6:
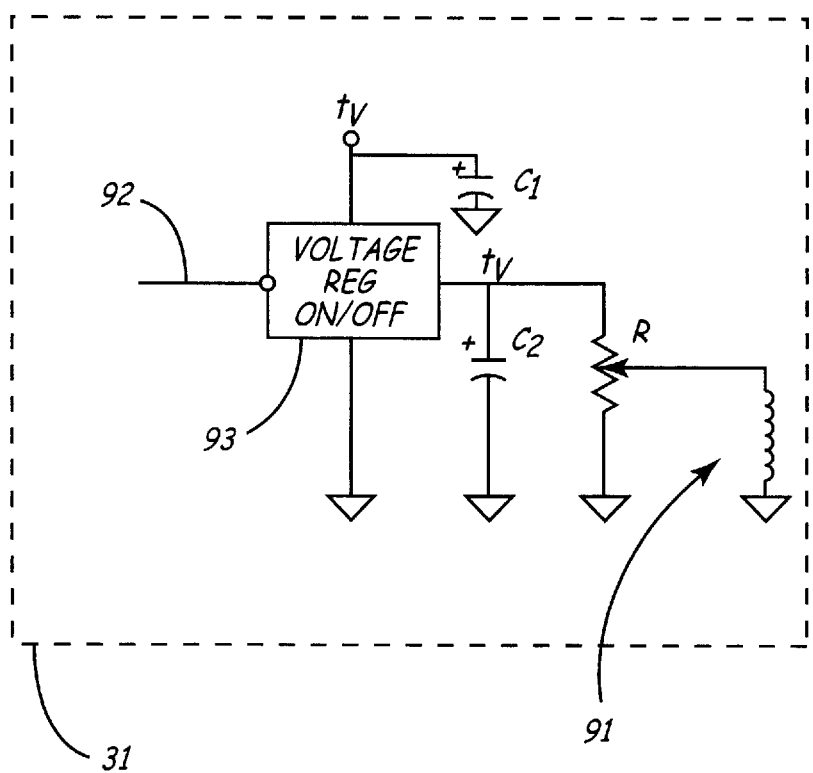
FIG. 6 is one illustrative embodiment of a tactile feedback generation device according to the present invention.

The tactile feedback generation device 90, as shown in FIG. 3, and the tactile feedback generation devices as described with reference to the other figures, may be provided in any number of manners. For example, as shown in FIG. 6, tactile feedback generation device 90 is provided by control of a vibrating motor 91 which is mechanically coupled to the housing 31 of the communication head 30 so as to impart motion or vibration to the communication head 30. For example, various vibrating motors have been used in the paging industry such as described in U.S. Pat. No. 4,794,392 to Selinko, entitled "Vibrator Alert Device for a Communication Receiver." The vibrating motor 91 is controlled by a control signal 92 applied to a voltage regulator 93 which turns the vibrating motor 91 on and off. When the vibrating DC motor begins to vibrate, the user is provided with information regarding the positioning of the communication head 30 relative to the implanted medical device 12 as described herein.

It will be recognized that other forms of generating tactile feedback may also be used. For example, piezoelectric devices may be activated to provide for vibration, an electric solenoid may be activated for providing vibration, or a relay contact may be chattered to also provide for vibratory or tactile feedback. As such, one skilled in the art will recognize that any number of vibration devices may be employed in accordance with the present invention such that tactile feedback may be used to indicate the validity of a communication channel between the external communication device 15 and the implanted medical device 12.

All patents and references cited herein are incorporated in their entirety as if each were incorporated separately. This invention has been described with reference to illustrative embodiments and is not meant to be construed in a limiting sense. As described previously, one skilled in the art will recognize that various other illustrative techniques for using tactile feedback in the positioning of a communication head relative to an implantable medical device may be implemented according to the present invention. Various modifications of the illustrative embodiments, as well as additional embodiments of the invention, will be apparent to persons skilled in the art upon reference to this description.

What is claimed is:

1. A communication device for establishing a communication link with an implantable medical communication device having a transceiver circuit, the device comprising:

a first transceiver circuit coupled to an external communication device;

a hand-held communication head coupled to the first transceiver circuit to establish a communication link between the transceiver circuit and a second transceiver circuit coupled to the implantable medical device;

a tactile feedback generation device coupled to the communication head and providing a tactile response feedback in response to detection of a valid communication link between the first transceiver circuit and the second transceiver circuit; and control circuitry operable to detect the valid communication link and upon detection of the valid communication link produce an activation signal;

wherein said tactile feedback generation device producing vibratory motion transmitted through the communication head in response to the activation signal, the vibratory motion produced being modified as a function of differing signal strengths between the first transceiver circuit and the second transceiver circuit and wherein the first transceiver comprises an automatic gain control amplification stage providing an adjustment in gain based on an inverse relationship to the signal strength between the first transceiver circuit and the second transceiver circuit, and wherein the control circuitry comprises an amplifier providing a drive signal to the tactile feedback generation device to modify the vibratory motion based upon the gain adjustment provided by the automatic gain control amplification stage.

2. The device of claim 1, wherein the external communication device includes a patient activation apparatus for the implantable medical device.

3. The device of claim 1, wherein the tactile feedback generation device includes a vibrating motor.

4. The device of claim 1, wherein the tactile feedback generation device includes a piezoelectric device.

5. The device of claim 1, wherein the tactile feedback generation device includes an electrical solenoid.

6. The device of claim 1, wherein the tactile feedback generation device includes a relay contact.

7. A communication device of claim 1 wherein the control circuitry comprises means for controlling and determining successful completion of a handshake sequence between the between the first transceiver circuit and the second transceiver circuit in order to detect that a valid communication link has been established.

8. A communication device of claim 1 wherein the control circuitry comprises means for controlling the tactile feedback generation device to discontinue tactile feedback after a predetermined period of time during which the valid communication link is sustained.

9. A communication device of claim 1 wherein the control circuitry comprises means for controlling activation of an additional tactile feedback generation device to provide an additional indicator signal when the valid communication link has been established.

10. A communication device of claim 1 wherein the first transceiver and the communication head are coupled to a programmer for the implantable medical device.

* * * * *